United States Patent
Currie

(10) Patent No.: US 11,896,041 B2
(45) Date of Patent: Feb. 13, 2024

(54) DEVICE AND METHOD FOR PASTEURIZING AND/OR STERILIZING PARTICULATE MATERIAL

(71) Applicant: BÜHLER AG, Uzwil (CH)

(72) Inventor: Alasdair Currie, London (GB)

(73) Assignee: BÜHLER AG, Uzwil (CH)

( * ) Notice: Subject to any disclaimer, the term of this patent is extended or adjusted under 35 U.S.C. 154(b) by 793 days.

(21) Appl. No.: 16/971,160

(22) PCT Filed: Feb. 20, 2019

(86) PCT No.: PCT/EP2019/054243
§ 371 (c)(1),
(2) Date: Aug. 19, 2020

(87) PCT Pub. No.: WO2019/162343
PCT Pub. Date: Aug. 29, 2019

(65) Prior Publication Data
US 2021/0000145 A1    Jan. 7, 2021

(30) Foreign Application Priority Data
Feb. 20, 2018   (EP) ..................... 18157701

(51) Int. Cl.
*A23L 3/26*     (2006.01)
*A23B 9/06*     (2006.01)
(Continued)

(52) U.S. Cl.
CPC .................... *A23L 3/26* (2013.01);
*A23B 9/06* (2013.01); *A61L 2/087* (2013.01);
*A61L 2/26* (2013.01);
(Continued)

(58) Field of Classification Search
CPC .. A23L 3/26; A23L 3/263; A23B 9/06; A23V 2002/00; A61L 2/087; A61L 2/26;
(Continued)

(56) References Cited

U.S. PATENT DOCUMENTS

| 4,112,307 A * | 9/1978 | Foll ................. H01J 33/04 250/492.3 |
| 4,631,444 A * | 12/1986 | Cheever ............ H01J 5/18 250/492.3 |

(Continued)

FOREIGN PATENT DOCUMENTS

| DE | 195 18 623 A1 | 11/1996 |
| EP | 0 705 531 B1 | 6/1997 |

(Continued)

OTHER PUBLICATIONS

European Search in corresponding European Application No. 18157701.6 dated Aug. 24, 2018.
(Continued)

*Primary Examiner* — Jennifer Wecker
*Assistant Examiner* — Brady C Pilsbury
(74) *Attorney, Agent, or Firm* — Finch & Maloney PLLC

(57) ABSTRACT

A device(s) and method for pasteurizing and/or sterilizing particulate material using an electron beam. The device (10) includes at least one electron source (20) for generating an electron beam, a treatment zone (19) in which the material, particularly a freely falling material, can be pasteurized and/or sterilized by the electron beam, and a material channel (21) arranged in the region of the treatment zone (19) in which the material can be pasteurized and/or sterilized by the electron beam. A planar protective element (23), which is at least partially permeable by the electron beam, is arranged between the electron source (20) and the material channel (21). The device (10) includes a holding frame (120) which holds the protective element (23) and which has a cavity (121) through which a cooling fluid can flow.

21 Claims, 7 Drawing Sheets

Figure 1:
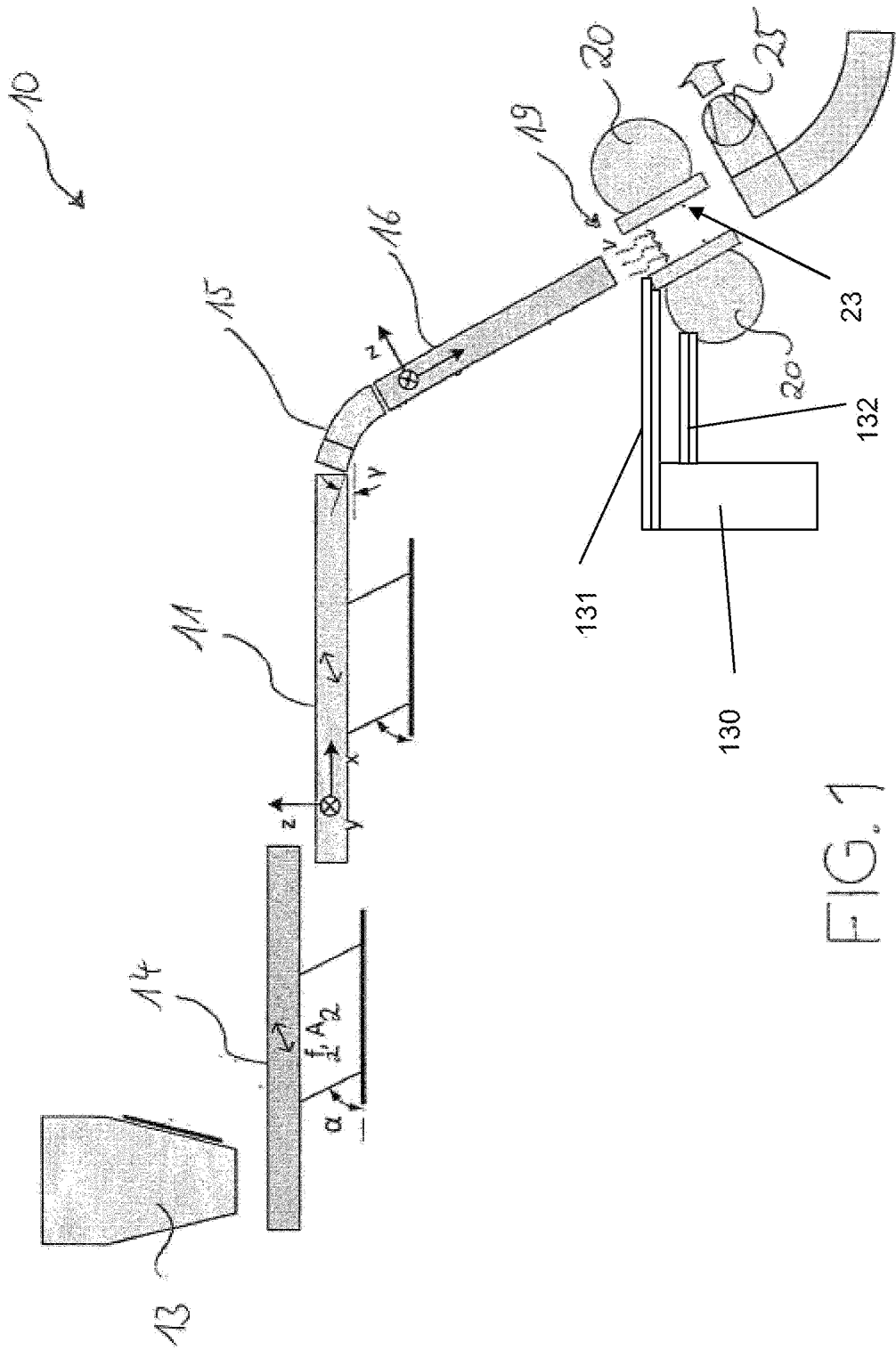

(51) Int. Cl.
*A61L 2/08* (2006.01)
*A61L 2/26* (2006.01)
*H01J 37/06* (2006.01)

(52) U.S. Cl.
CPC .......... *H01J 37/06* (2013.01); *A23V 2002/00* (2013.01); *A61L 2202/11* (2013.01); *A61L 2202/122* (2013.01); *A61L 2202/14* (2013.01); *H01J 2237/002* (2013.01)

(58) Field of Classification Search
CPC .......... A61L 2202/11; A61L 2202/122; A61L 2202/14; H01J 33/04; H01J 37/06; H01J 2237/002; G21K 5/08
See application file for complete search history.

(56) References Cited

U.S. PATENT DOCUMENTS

| | | | | |
|---|---|---|---|---|
| 4,734,586 | A * | 3/1988 | Crist | H01J 33/00 250/503.1 |
| 5,801,387 | A * | 9/1998 | Nablo | H01J 33/00 250/398 |
| 6,724,003 | B1 * | 4/2004 | Doi | B01D 53/60 250/492.3 |
| 2004/0089820 | A1 * | 5/2004 | Rangwalla | G21K 5/10 250/492.3 |
| 2015/0216106 | A1 * | 8/2015 | Kotte | A01C 1/08 250/434 |
| 2015/0306261 | A1 * | 10/2015 | Naslund | H01J 33/00 250/354.1 |
| 2017/0213689 | A1 * | 7/2017 | Abe | H01J 37/141 |

FOREIGN PATENT DOCUMENTS

| | | |
|---|---|---|
| EP | 1 080 623 A1 | 3/2001 |
| JP | S50-46803 A | 4/1975 |
| JP | H11 133193 A | 5/1999 |
| JP | 2000 304900 A | 11/2000 |
| JP | 2002 078472 A | 3/2002 |
| JP | 2002 085029 A | 3/2002 |
| JP | 2003-156599 A | 5/2003 |
| JP | 3 569329 B2 | 9/2004 |
| JP | 2004-337192 A | 12/2004 |
| JP | 3 777080 B2 | 5/2006 |
| JP | 2007010450 A | 1/2007 |
| JP | 50-46803 B2 | 7/2012 |
| WO | 2018/036899 A1 | 3/2018 |
| WO | 2018/036900 A1 | 3/2018 |

OTHER PUBLICATIONS

International Search Report in corresponding PCT application No. PCT/EP2019/054243 dated Apr. 11, 2019.
Written Opinion from corresponding PCT application No. PCT/EP2019/054243 dated Apr. 11, 2019.
Observation by Third Party Submitted Aug. 16, 2021.

* cited by examiner

DEVICE AND METHOD FOR PASTEURIZING AND/OR STERILIZING PARTICULATE MATERIAL

The present invention relates to devices and processes for pasteurizing and/or sterilizing particulate material by means of an electron beam.

Particulate material is here and in the following referred to as goods consisting of grains and/or flakes, whereby the particles may have, for example, a spherical, plate-like or angular shape. They can also be ground particles. Pasteurization and/or sterilization can, for example, kill or render harmless microorganisms, at least to a large extent. In particular, a reduction of harmful micro-organisms by at least one, preferably at least five, particularly preferably at least seven orders of magnitude can be achieved.

A generic device is known from EP 1 080 623 B1, for example. This device contains vibratory conveyors with which seeds can be separated into a transparent curtain. This curtain is then passed through an electron field generated by an electron accelerator, which can, for example, cause the seed to be sterilized. A grid is used to keep the seeds away from an exit window of the electron accelerator.

From the U.S. Pat. No. 5,801,387 A another generic device is known. In this invention, a particulate material is dosed into a horizontal air stream with a vibratory feeder and then exposed to an electron beam. The treatment zone is separated from the electron beam source by a window.

Another device is known from EP 0 705 531 B1, which introduces the seed into a process chamber by means of a dosing device not described in detail, in which it falls vertically through an electron beam. A cooling gas is used to cool the beam exit window. This gas is led past the beam exit window through a nozzle system with an inlet and an outlet.

Further devices and processes for pasteurising and/or sterilising particulate material are disclosed in the applicant's international patent application PCT/EP2017/070842. The devices contain at least one electron source for generating an electron beam and a treatment zone in which the goods can be pasteurized and/or sterilized by means of the electron beam.

The PCT/EP2017/070842 discloses a device having a material channel in a region of the treatment zone in which the material can be pasteurized and/or sterilized by means of the electron beam. The device has at least one secondary channel through which a fluid can flow, which extends at least partially between the electron source and the material channel and is fluid-separated from the material channel. The fluid flowing through the secondary channel can be used to cool the electron source and in particular an outlet window of the electron source.

When cooling fluid passes the outlet window of the electron source, it is mainly the air surrounding the window that is cooled and thus indirectly also the outlet window. The cooling is therefore indirect and depends on the flow conditions in the vicinity of the exit window.

The PCT/EP2017/070842 also shows a protective film which is placed between the electron source and the material channel and is at least partially transparent to the electron beam. This protective film preferably separates the material channel from the secondary channel. The secondary channel is also preferably arranged at least partially between the electron source and the protective film.

The fluid in it thus serves to cool the protective film and is exposed to the electron beam during operation of the device and can thus be heated.

Also revealed is a cassette for insertion into a device for pasteurising and/or sterilising particulate material.

It is the task of the present invention to overcome the disadvantages known from the prior art. In particular, devices and methods shall be provided which allow a reliable, direct and/or as homogeneous as possible cooling of the outlet window.

The task is solved by a device for pasteurizing and/or sterilizing particulate material. "Pasteurisation" or "pasteurisation" in this context means in particular a reduction of the bacterial count by log 5, preferably log 6, particularly preferably log 7 or more. "Sterilisation" or "sterilisation" is understood to mean in particular complete sterilisation.

The device contains at least one electron source for generating an electron beam.

The at least one electron source may be known per se. The device may contain one or more electron sources. If there are several electron sources, they may be arranged opposite one another or in succession with respect to the direction of flow of the material.

The device also contains a treatment zone in which the material can be pasteurized and/or sterilized by means of the electron beam.

In particular, the material can be pasteurized and/or sterilized in a free-falling manner. The material is described as "free-falling" when the trajectories of the individual particles of the material are determined solely by their velocity, the force of gravity acting on them and, where appropriate, a process gas with which the material is surrounded. In particular, the particles of the material do not slide on a surface through the treatment zone. The process gas may be air, for example. However, it is also conceivable that a gas which prevents ozone formation, such as nitrogen, is used as the process gas.

It is also conceivable and within the scope of the invention that the device has several treatment zones. In this way an even more effective pasteurisation and/or sterilisation can be achieved. Alternatively, the material can be passed several times through one and the same treatment zone.

The device contains a material channel arranged in the area of the treatment zones, in which the material can be pasteurized and/or sterilized by means of the electron beam.

By means of the electron beam not only the material itself can be treated, but also any process gas surrounding the material and/or other particles flowing with the material, such as dust.

The device comprises a flat protective element arranged between the electron source and the material channel. The protective element is at least partially permeable to the electron beam.

The protective element contains in particular a metal, preferably titanium, preferably it consists of metal.

The protective element prevents the material from reaching the electron source and protects the electron source, in particular the electron source exit window itself, which is covered with a thin and correspondingly fragile film.

According to the invention, the device contains a holding frame which holds the protective element and which has a cavity through which a cooling fluid can flow.

The holder is designed in such a way that there is a connection between the protective element and the holding frame which allows good thermal conductivity. The protective element is in direct contact with the holding frame in particular.

The protective element can be clamped in the holding frame, clamped in the holding frame, glued or welded onto the holding frame.

Preferably, the holding frame is detachably attached to the device, so that the holding frame can be removed and, if necessary, also replaced for replacement of the protective element.

A pressure measurement can be used to determine whether the protective element is still intact, especially if it is a protective film.

The holding frame surrounds the protective element at least partially. Preferably, the holding frame surrounds the protective element on a considerable part of its circumference in such a way that heat exchange is distributed as evenly as possible over the circumference.

The cavity is used to conduct a cooling fluid, i.e. a cooling gas or a cooling liquid, on the holding frame or through the holding frame. The cavity is arranged so that a good thermal contact between the cooling fluid and the holding frame can be established.

The holding frame can be arranged so that it is not in the electron beam. The cooling fluid is thus guided around the electron beam and is therefore not directly exposed to the electron beam and does not experience any direct heating.

Preferably, the holding frame is made of a material that is not or only slightly permeable to an electron beam.

The process gas can serve as a cooling fluid.

The cavity is preferably fluid-separated from the treatment zone. Fluid separation in this case means that neither the fluid from the cavity can enter the material channel nor the material and any process gas surrounding the material can enter the cavity from the material channel. The cooling fluid is then freely selectable and does not have to be matched to the material.

The cavity is preferably, except for at least one inlet and at least one outlet, designed as a closed system, e.g. as a tube, i.e. as an essentially cylindrical hollow body, which can be completely surrounded by the holding frame.

The cavity can also be formed in a tube which rests against the holding frame.

The cooling fluid flowing through the holding frame preferably does not come into contact with the protective element. It can therefore be cooled with liquid and with rapidly transported cooling fluid, as there is no risk of the protective element being set in vibration. Rapidly transported cooling fluid can quickly dissipate the heat.

The cavity is preferably part of a cooling circuit through which a cooling fluid flows, and in which the cooling fluid cools down again in particular.

The device may include at least one pump to drive cooling fluid to the protective element and/or the electron source.

The cavity may be partially open to the environment. It may be formed as a groove in the support frame.

The cavity may, for example, be formed by baffles which guide the cooling fluid past the holding frame and/or the holding frame.

The holding frame is tempered by the cooling fluid. The protective element is thus cooled. The cooling is independent of flow conditions. The cooling fluid can travel short distances in the cavity and cooling is therefore fast and effective if good thermal contact between the holding frame and the protective element is ensured.

The protective element can be designed as a grid, preferably the protective element is designed as a protective foil, which provides safety for the electron source and is easier to clean.

The protective foil is preferably made of a metal, such as titanium, aluminium, gold, silver or copper. The metal can also be an alloy. In some applications the protective film may be coated. Alternatively, it is also conceivable and within the scope of the invention that the protective film consists of a plastic.

On the one hand, the cooling of the holding frame has the effect of cooling the protective element. At the same time, it prevents the holding frame from acting as a heat accumulator, which in turn supplies heat to the protective element if it is cooled in some other way, for example via a secondary channel.

The cooling of the holding frame is used for surface cooling of the holding frame, which should preferably be kept at a temperature below 200° C. to avoid the risk of dust self-ignition and to reduce dust deposits.

A protective element that can be cooled well can also cool the space surrounding the protective element. The service life of the protective element is extended by the cooling.

In a beneficial extension of the invention, the device has at least one secondary channel through which a fluid can flow, which runs at least partially between the electron source and the material channel and is fluidly separated from the material channel.

The fluid flowing through the secondary channel can be used to cool the electron source and in particular an outlet window of the electron source.

Alternatively or additionally the fluid can be used to remove ozone generated by the electron beam. Neither this cooling nor this removal of ozone from the secondary channel has any influence on the fluid flow in the material channel.

Fluid separation in this case means that neither the fluid can enter the material channel from the secondary channel nor the material and any process gas surrounding the material can enter the secondary channel from the material channel. This prevents damage or contamination of the electron source, in particular an electron source outlet window, by the material. The fluid can be a liquid or a gas, such as air.

The cavity and the secondary channel may be fluid-separated. However, there may also be a fluid connection, so that cooling fluid flowing through the secondary channel also flows through the cavity.

In particular, the protective element can separate the material channel from the secondary channel. The fluid flowing through the secondary channel then comes into contact with the protective element and can be used for additional cooling of the protective element.

Alternatively or additionally, the secondary channel can be at least partially located between the electron source and the protective element. The fluid flowing through the side channel can then cool the area surrounding the electron source and thus the electron source, and can also contribute to cooling the protective element.

In an advantageous further development of the device, the protective element, in particular the protective foil, contains at least one thickening. Preferably the protective element contains several thickenings.

The thickenings extend along a main plane of the protective element and substantially perpendicular to a direction of flow of the material.

The thickenings stabilize the protective element so that it can also withstand impacts from sharp-edged material.

The thickenings can also be used to define the treatment window, i.e. to define more precisely the area of the treatment zone where the material is pasteurized and/or sterilized by means of the electron beam.

A protective film with thickenings combines the advantages of a film and a grid.

The device may include separate cooling circuits for the electron source and the protective element, each of which has a cooling device for cooling the cooling fluid.

Advantageously, the device contains a cooling device with two interconnected cooling circuits, whereby a cooling fluid can be supplied to the holding frame by means of a first cooling circuit and to the electron source by means of a second cooling circuit.

Particularly good cooling can be achieved if the device contains at least one fan directed at the protective element for further cooling of the protective element.

The cooling gas moved by the fan can be led directly from the fan to the protective element or, for example, be conducted to the protective element through the secondary channel.

With particular advantage, the device contains a cassette holder for receiving a cassette, the cassette at least partially delimiting the material channel and in particular the at least one secondary channel. The cassette may contain the holding frame or a receptacle for the holding frame. The holding frame may be detachably received or receivable in the cassette.

Preferably, holding frames for two protective elements are an integral part of the cassette and/or are designed in one piece with the cassette.

It is particularly advantageous for the cassette to contain the complete material channel and in particular to include holding frames for two opposite protective elements. The entire treatment zone can be removed and/or replaced for maintenance or cleaning purposes, for example.

The cassette preferably comprises the cavity, which is designed as a continuous tube and serves to cool both protective elements and the cassette.

The cassette may contain a pressure measuring device to determine whether the protective element is still intact.

Furthermore, the electron source is movable, in particular pivotable and/or displaceable, relative to the cassette holder in such a way that it can be moved away from the cassette. This simplifies access to the cassette and thus also to the protective element. The protective element can therefore be replaced more easily if it has been soiled or damaged by the goods. To do this, the protection element is removed from the cassette together with the holding frame, for example.

The cassette can preferably be inserted into a cassette holder of the device in a direction transverse to the direction of material flow. For this purpose, the cassette holder of the device can include a frame with a guide in which the cassette slides and in which seals are located.

The cassette is advantageously equipped with connection pieces for connecting the cavity to a cooling circuit.

The cassette is advantageously equipped with fluid connectors for coupling to a cooling circuit.

Another aspect of the invention relates to a cassette for insertion into a cassette receptacle of a device for pasteurizing and/or sterilizing particulate material, which contains at least one electron source for generating an electron beam. In particular, it may be a device as described above. The cassette contains boundary surfaces for at least partially bounding a material channel and in particular at least one secondary channel of the device. The cassette contains at least one support frame for a protective element or a holder for at least one support frame. The cassette is preferably designed as described above.

The cassette can be inserted into the cassette receptacle in such a way that the device has a material channel in the region of a treatment zone, in which the material can be pasturised and/or sterilised by means of the electron beam, and that the device has in particular at least one secondary channel through which a fluid can flow, which extends at least partially between the electron source and the material channel and is fluid-separated from the material channel. The boundary surfaces of the cassette then at least partially bound the material channel and in particular the at least one secondary channel.

The invention also comprises a device as described above with a cassette holder and a cassette inserted therein as described above.

In the area of the treatment zone, the material flows through a material channel in which it is pasteurized and/or sterilized by means of the electron beam.

According to this independent aspect, a fluid flows through the cavity and in particular through at least one secondary channel which runs at least partially between the electron source and the material channel and is fluid-separated from the material channel. As already mentioned, this fluid, which can be a liquid or a gas, can be used to remove ozone which has been generated by the electron beam.

Alternatively or additionally, the fluid can also be used to cool the electron source, especially an outlet window, for example in a connected cooling circuit or when flowing through a secondary channel.

The fluid can flow through the secondary channel parallel or opposite to the direction of flow of the material. A gas that prevents ozone formation, such as nitrogen, can be used as the fluid.

The fluid flowing through the secondary channel and/or through the cavity can be identical to or different from the process gas flowing in the material channel. However, other directions of flow of the fluid are also conceivable and are within the scope of the invention.

In the context of the present application, the terms "downstream" and "upstream" refer to the direction of flow of the particulate material when the device is operated as intended. Consequently, a first unit is considered to be downstream of a second unit when, when the device is operated as intended, the material passes through it after the second unit. Similarly, a first unit is considered to be upstream of a second unit if, when the device is operated correctly, the material passes through it before the second unit.

The device may also have one or more of the features disclosed to the applicant in the international patent application PCT/EP2017/070842 mentioned above:

I. Apparatus for pasteurising and/or sterilising particulate material, containing
   a preferably essentially horizontal first vibrating surface which can be excited to vibrate in order to convey and separate the material,
   at least one electron source for generating an electron beam,
   a treatment zone arranged downstream of the first vibrating surface, in which the material can be pasturised and/or sterilised, in particular in a free-falling manner, by means of the electron beam,
   wherein the first vibrating surface comprises a plurality of troughs in which the material can be conveyed and by means of which it can be separated.

II. Apparatus according to combination of features I,
   wherein the apparatus comprises an inclined chute surface downstream of the first vibration surface and upstream of the treatment zone, said surface being constructed and arranged to allow the material thereon to slide towards the treatment zone.

III. Apparatus according to combination of features II, wherein the sliding surface comprises at least one channel, preferably a plurality of channels, which is/are formed and arranged in such a way that the material can slide and be separated therein.
IV. Apparatus according to one of the combinations of features II and III,
wherein the sliding surface is inclined downwards with respect to a horizontal at an angle which is in the range of 45° to 85°, preferably 55° to 75°, particularly preferably 60° to 70°.
V. Apparatus according to one of the preceding combinations of characteristics,
wherein the apparatus has a deflecting surface downstream of the first vibration surface and upstream of the treatment zone, in particular upstream of the sliding surface, which is constructed and arranged in such a way that the material is deflected thereon and can slide from the first vibration surface to the sliding surface and/or in the direction of the treatment zone.
VI. Apparatus according to combination of characteristics V, wherein the deflecting surface comprises at least one channel, preferably a plurality of channels, which is/are constructed and arranged in such a way that the material can slide therein.
VII. Apparatus according to one of the preceding combinations of characteristics,
wherein the apparatus has a substantially flat and preferably substantially horizontally oriented second vibration surface upstream of the first vibration surface, which is excitable to vibrations.
VIII. Apparatus for pasteurising and/or sterilising particulate material, comprising
at least one electron source for generating an electron beam,
a treatment zone in which the material can be pasturised and/or sterilised, in particular in a free-falling manner, by means of the electron beam,
in particular device according to one of the preceding combinations of features,
wherein the device has a material channel in the region of the treatment zone, in which the material can be pasturised and/or sterilised by means of the electron beam, the apparatus having at least one secondary channel through which a fluid can flow, which extends at least partially between the electron source and the material channel and is fluid-separated from the material channel.
IX. Apparatus according to combination of features XIII, wherein a protective film which is at least partially permeable to the electron beam and in particular consists of a metal, preferably titanium, is arranged between the electron source and the material channel.
X. Apparatus according to feature combination IX, whereby the protective film separates the material channel from the secondary channel.
XI. Apparatus according to one of the feature combinations IX and X, wherein the secondary channel is at least partially located between the electron source and the protective film.
XII. Apparatus according to one of the feature combinations IX to XI, the apparatus having a cassette receptacle for receiving a cassette, the cassette at least partially delimiting the material channel and the at least one secondary channel and containing a film receptacle for receiving the protective film, and the electron source being arranged movably, in particular pivotably and/or displaceably, relative to the cassette receptacle in such a way that it can be moved away from the cassette.
XIII. Apparatus according to feature combination XII, wherein a cassette is inserted in the cassette receptacle, which at least partially defines the material channel and the at least one secondary channel and contains a film receptacle from which the protective film is received.
XIV. Apparatus according to one of the preceding combinations of characteristics, wherein the apparatus includes a suction device for sucking off process gas surrounding the material downstream of the treatment zone.
XV. Apparatus according to one of the preceding combinations of characteristics,
wherein the apparatus downstream of the treatment zone comprises a sorting device which contains a measuring unit and an ejection unit which are designed in such a way that individual particles of the material can be ejected by means of the ejection unit on the basis of at least one characteristic of the particles measured by means of the measuring unit.
XVI. Apparatus according to one of the preceding combinations of characteristics, wherein the device has at least one gas outlet opening arranged downstream of the treatment zone for blowing a cleaning gas onto the material.

The material can be a foodstuff such as cereals such as soya, breakfast cereals, snacks, nuts such as dried coconuts, almonds, peanut butter, cocoa beans, chocolate, chocolate liquid, chocolate powder, chocolate chips, cocoa products, legumes, coffee, seeds such as pumpkin seeds, Trade spices (such as curcuma, especially in slices), tea mixtures, dried fruits, pistachios, dried protein products, bakery products, sugar, potato products, pasta, baby food, dried egg products, soy products such as soybeans, thickeners, yeasts, yeast extracts, gelatine or enzymes.

Alternatively, the material may be a pet food, such as pellets, feed for ruminants, poultry, aquatic animals (especially fish) or pets, or compound feed.

However, it is also conceivable and within the scope of the invention that the material may be a plastic such as PET, for example, in the form of flakes or pellets.

The problem is further solved by a method for pasteurising and/or sterilising particulate material with a device as described above. The process includes the following steps. An electron beam is generated by means of the electron source. Material, which in particular falls freely, is pasteurized and/or sterilized in the treatment zone by means of the electron beam. A cooling fluid is passed through the hollow space of the holding frame to cool the protective element.

The cooling fluid can have a temperature in the range of 15° C. to 43° C., preferably 25° C., when entering the hollow space. The temperature should be higher than 15° C. to avoid condensation, especially on the protective element. On exit, the temperature is in the range 30° C. to 50° C., preferably 36° C.

Advantageously, the cooling fluid is passed through the cavity with a volume flow in the range of 2-6 l/min m, preferably 4 l/min.

The cooling fluid can be air, nitrogen or water.

Furthermore, the process may have one or more of the features disclosed in the applicant's international patent application PCT/EP2017/070842 mentioned above:

XVII. Method for pasteurizing and/or sterilizing particulate material, in particular with an apparatus as disclosed above, comprising the following steps:
  a) conveying and separating the material by means of a preferably substantially horizontal first vibration surface which is excited to vibrations and has a plurality of channels in which the material is conveyed and by means of which it is separated,
  b) Generation of an electron beam,
  c) Pasteurisation and/or sterilisation of the material, in particular freely falling material, by means of the electron beam in a treatment zone.

XVIII. Method for pasteurising and/or sterilizing particulate material, in particular with a device as disclosed above, comprising the following steps:
  b) Generation of an electron beam,
  c) Pasteurisation and/or sterilisation of the material, in particular freely falling material, by means of the electron beam in a treatment zone,
  in particular a method according to the combination of characteristics of XVII,
  wherein the material flows in the region of the treatment zone through a material channel in which the material is pasturised and/or sterilised by means of the electron beam, characterised in that
  a fluid flows through at least one secondary channel which runs at least partially between the electron source and the material channel and is fluidly separated from the material channel.

XIX. Method according to the combination of characteristics XVIII,
  wherein the protective film separates the material channel from the secondary channel.

XX. Method according to one of the feature combinations XVIII and XIX,
  wherein the secondary channel is at least partially located between the electron source and the protective film.

XXI. Method according to one of the feature combinations XVII to XX,
  wherein the process gas surrounding the material is sucked off after pasteurisation and/or sterilisation, in particular at a suction speed which is 1 to 3 times, preferably 1 to 1.5 times the speed of the material during pasteurisation and/or sterilisation.

In the following, the invention is explained in more detail by means of several design examples and several drawings. Elements with the same function each have the same reference lines.

Thereby show

Figure 2:
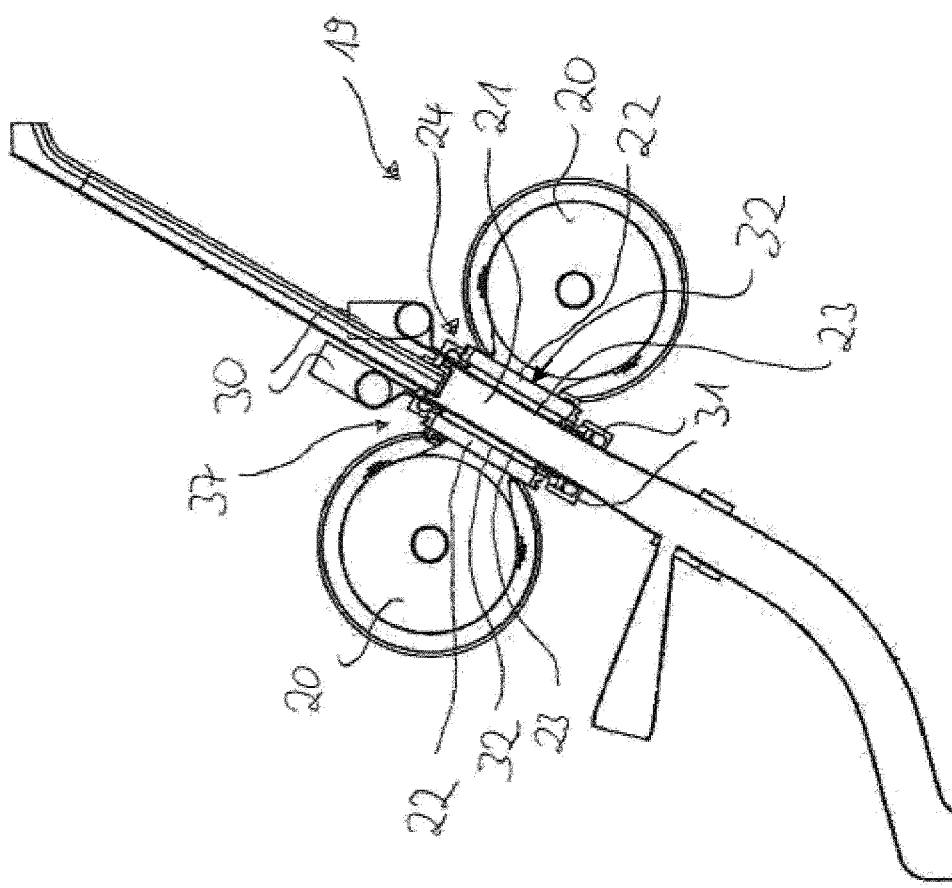
Figure 3:
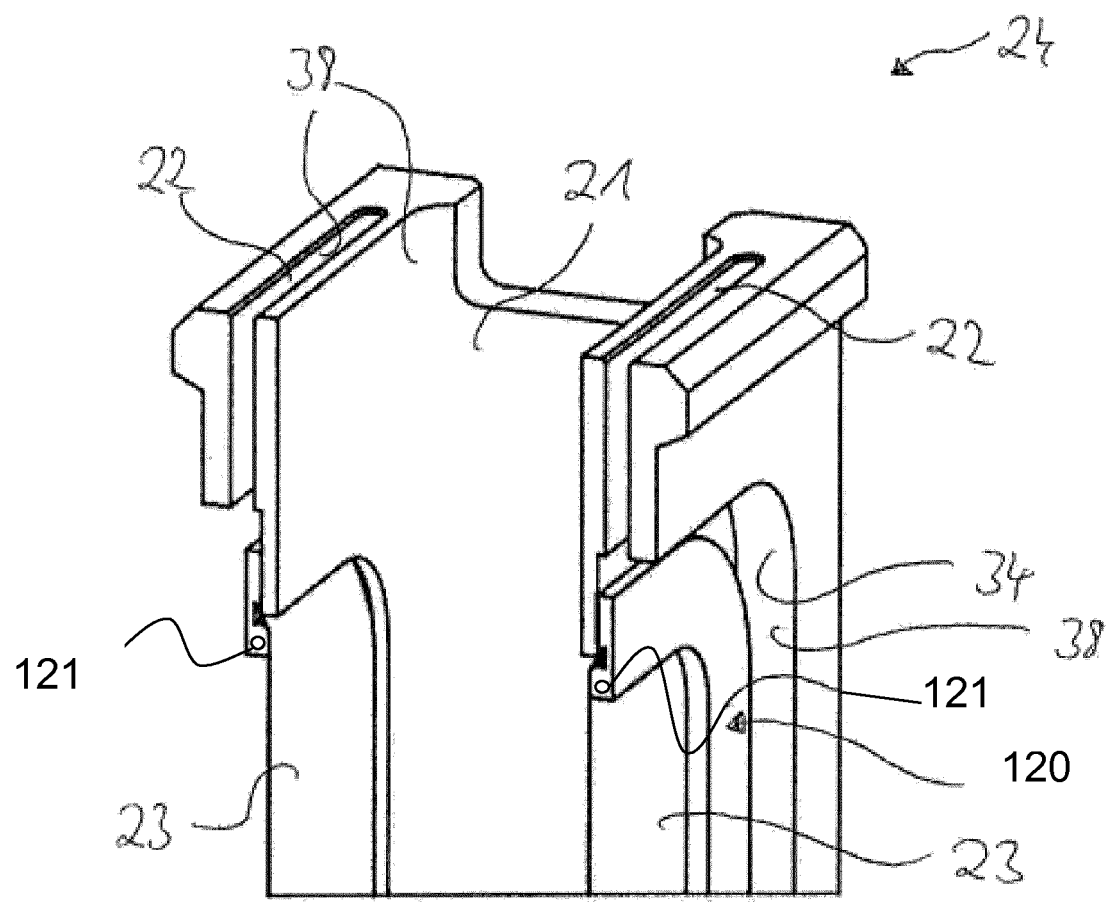
Figure 4:
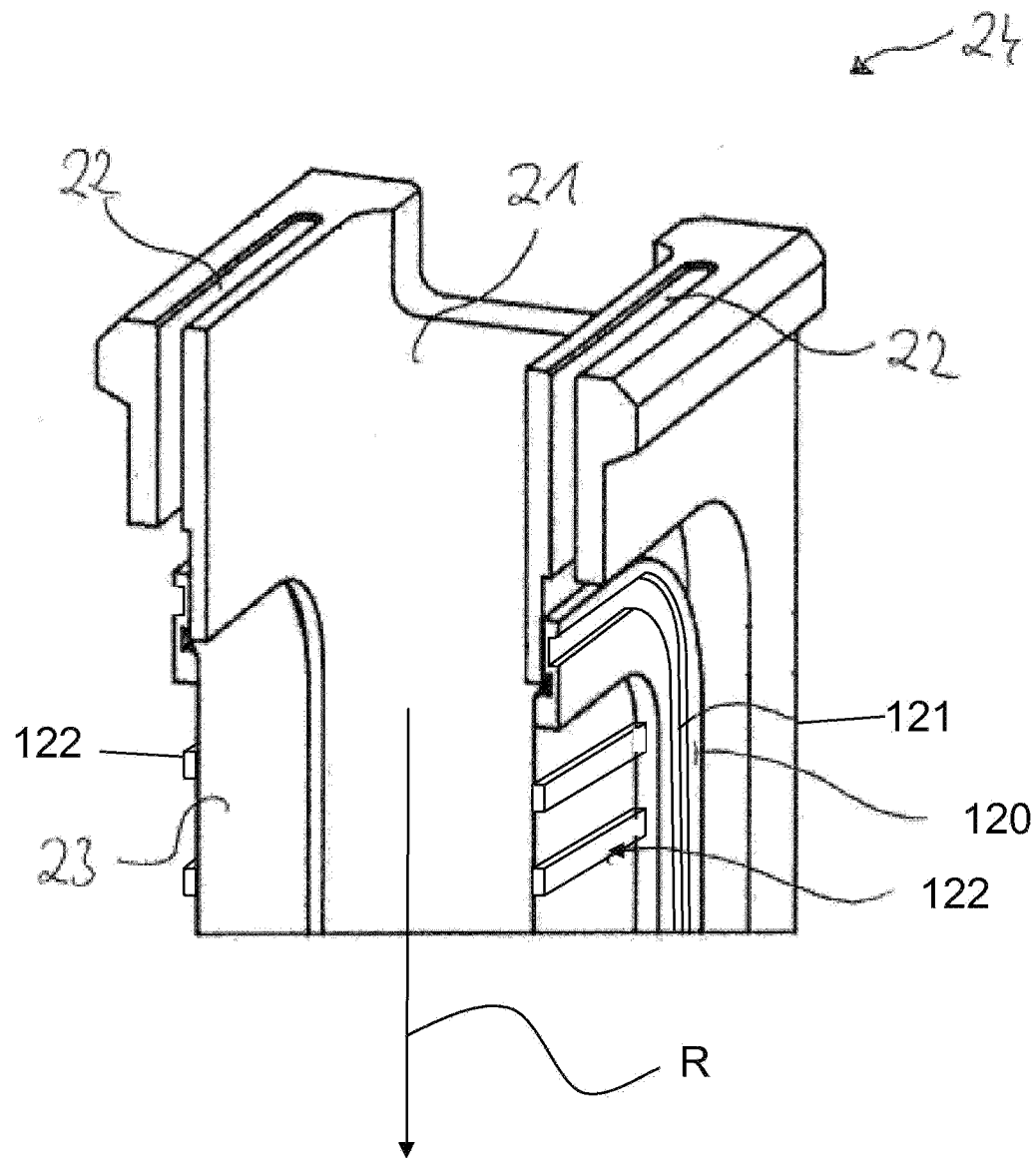
Figure 5:
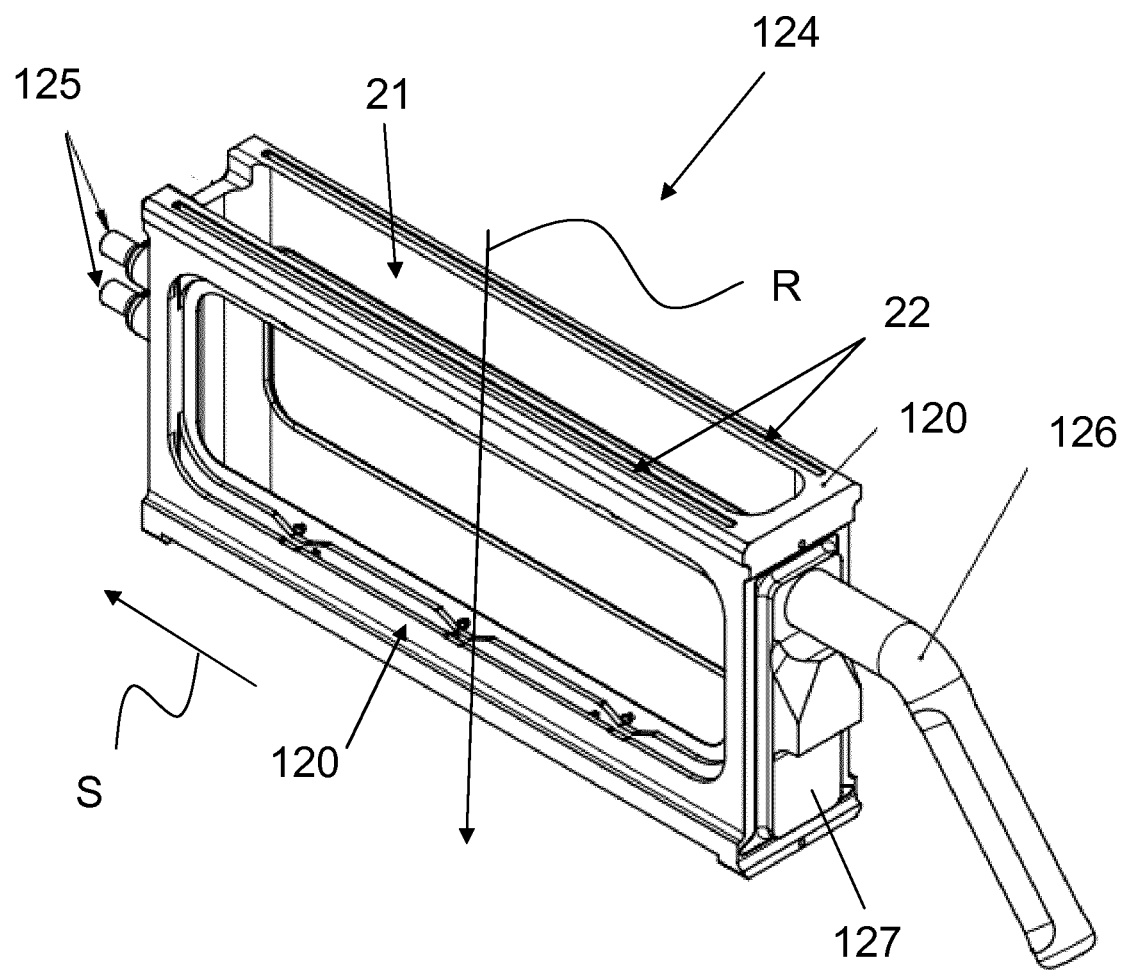
Figure 6:
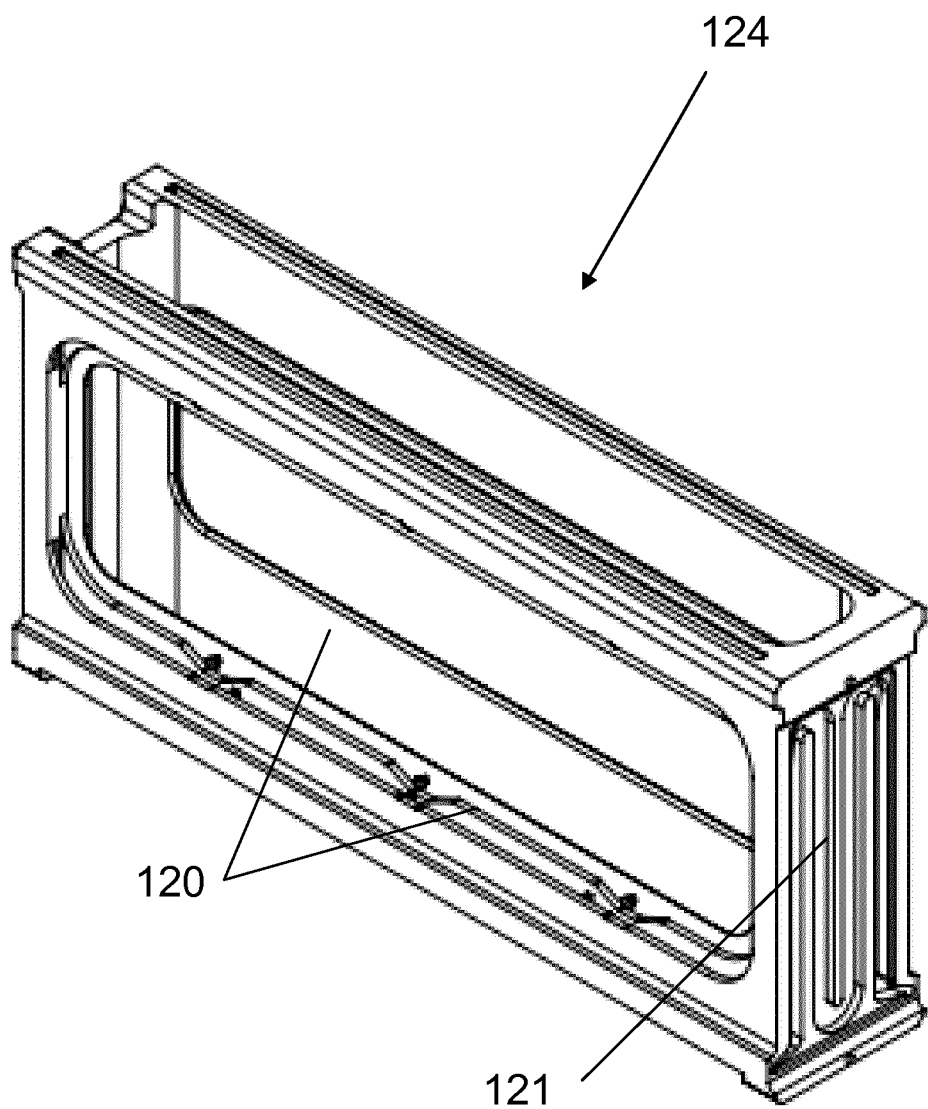
Figure 7:
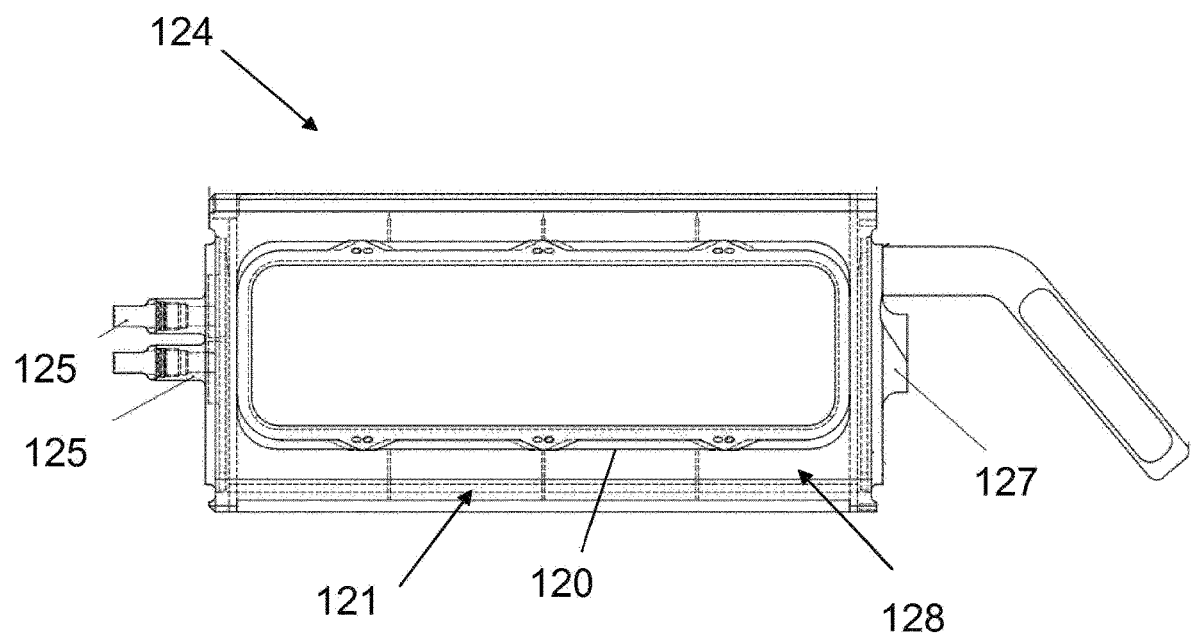

FIG. 1: a schematic side view of a device according to the invention;

FIG. 2: a side view of a treatment zone of the device of the invention;

FIG. 3: a perspective sectional detail view of a first example of a cassette according to the invention of the device according to the invention;

FIG. 4: a perspective sectioned detailed view of a second example of a cassette according to the invention of the device according to the invention;

FIG. 5: a first perspective section of a third example of a cassette according to the invention of the device according to the invention;

FIG. 6: a further perspective view of the third example of a cassette according to the invention of the device according to the invention;

FIG. 7: the third example of a cassette according to the invention of the device according to the invention in a sectional view.

The device 10 shown in FIG. 1 is intended for pasteurising and/or sterilising particulate material, such as a spice, sesame, almonds or peeled pistachios. It contains a dosing device 13, with which the material can be dosed onto a second vibrating surface 14. This second vibrating surface 14 can be used to control the throughput of the material and can also be used to pre-separate the material.

Downstream of the second vibrating surface 14, the device 10 contains a horizontally aligned first vibrating surface 11, which allows the material to be conveyed and separated further downstream.

Downstream of the first vibrating surface 11, the device 10 has a deflecting surface 15. This is designed and arranged in such a way that the material is deflected onto it and can slide from the first vibrating surface 11 to a sliding surface 16. The deflecting surface 15 is adapted to the material and the first vibrating surface 11 in such a way that the particles of the material are guided on a parabolic path substantially downstream on which they would also fall solely under the action of gravity.

Even further downstream, the device 10 contains a treatment zone 19, where the material is pasteurized and/or sterilized in a free-falling manner by means of an electron beam generated by two electron sources 20 opposite each other.

The apparatus 10 further contains an extraction device 25 with which process gas surrounding the material can be extracted downstream of the treatment zone 19.

For pasteurizing and/or sterilizing particulate material by means of this apparatus 10 the following steps are carried out:

By means of the second vibrating surface 14 the throughput of the material is controlled and a pre-singulation takes place. By means of the electron sources 20, an electron beam is generated in a further step. In a further step, the freely falling material is pasteurized and/or sterilized by the electron beam in the treatment zone 19.

In the case of spices, the material moves advantageously at a speed in the range of 1 m/s to 5 m/s, preferably from 2 m/s to 4 m/s, particularly preferably from 2 m/s to 3 m/s, for example from 2.5 m/s through the treatment zone 19. This speed can be adjusted by the length and angle of inclination and the length of the sliding surface 16.

The higher the speed of the material, the greater the attainable throughput. In free fall the speed is independent of the throughput, so that throughputs in the range of 100 kg/h to 1000 kg/h can be achieved at the same speed, for example.

The throughput can depend on the vibration of a vibrating surface 11, 14 and the dimensions and orientations of the deflecting surface 15 and the sliding surface 16. In addition, as the speed of the material increases, the probability of collision of the particles with the electron source 20 or a protective element 23 decreases. On the other hand, the speeds must not be too high so that the material remains in the electron beam long enough to be pasteurized and/or sterilized.

The electrons of the electron beam have an energy in the range of 80 keV to 300 keV, preferably 140 keV to 280 keV, particularly preferably 180 keV to 260 keV, for example at 250 keV. Lower electron energies would not produce sufficient pasteurisation and/or sterilisation. Higher electron energies could not achieve significantly higher degrees of pasteurisation and/or sterilisation.

In treatment zone 19, the electron beam has a mean current density in the range of $10^{15}$ $s^{-1} \cdot cm^{-2}$ to $2.77 \cdot 10^{15}$ $s^{-1} \cdot cm^{-2}$. The material is exposed to the electron beam for a treatment time which is in the range of 5 ms to 25 ms and can be 15 ms, for example. This is because a certain minimum treatment time is required for sufficient pasteurization and/or sterilization. Too long treatment times have not shown a significantly increased degree of pasteurisation and/or sterilisation and would also reduce throughput.

As a result, the material is exposed to radiation doses ranging from 1 kGy to 45 kGy, preferably from 8 kGy to 30 kGy, particularly preferably from 10 kGy to 16 kGy, and can be as high as 12 kGy, for example.

After pasteurisation and/or sterilisation in treatment zone 19, the process gas surrounding the material is extracted by means of the extraction device 25 at a preferred extraction speed of 1 to 1.5 times the speed of the material during pasteurisation and/or sterilisation.

The device 10 also includes a cooling device 130, which supplies two cooling circuits. One cooling circuit 132 supplies cooling fluid to the electron source 20, another cooling circuit 131 supplies cooling fluid to the protective element 23 which separates the treatment zone 19 from the electron sources 20.

FIG. 2 shows a detailed view of treatment zone 19. In the area of the treatment zone 19, the device 10 has a cassette 24 arranged between outlet windows 32 of the electron sources 20. The cassette 24 is inserted in a cassette holder 37. The cassette 24 contains two holding frames 120 (see FIG. 3), each for a protective element 23 made of titanium, which is partially transparent to the electron beams. The cassette 24 contains a number of boundary surfaces 38 (see FIG. 3) which, together with the protective foils 23, define a material channel 21 in which the material can be pasteurized and/or sterilized by means of the electron beams.

Furthermore, the device 10 contains two secondary channels 22 in the area of the treatment zone 19, which are limited in an operating position by the boundary surfaces 38 of the cassette 24 shown in FIG. 3, the protective foil 23 and the exit windows 32 of the electron sources 20 and thus run between the material channel 21 and the electron sources 20.

The material channel 21 is fluidly separated from the secondary channels 22, among other things by the protective element. Air can be introduced through inlet openings 30, which can flow through the secondary channels 22 parallel to the direction of flow of the material. Downstream, air can exit from outlet openings 31. This air flow allows, on the one hand, the removal of ozone generated by the electron beams and, on the other hand, cooling of the electron sources 20 and, in particular, their exit windows 32.

FIG. 3 shows an even more detailed, sectional and perspective view of a first example of a cassette 24, in which the material channel 21, the two secondary channels 22 and the two protective elements 23 are visible.

The material channel 21 is fluidly separated from the secondary channels 22 by the two protective elements 23.

The protective elements 23 are clamped in a holding frame 120. A recess 34 is formed on each side of the cassette 24 facing away from the material channel 21. In the operating position of the device 10, these recesses are closed by outlet windows 32 of the electron sources 20 and through which the electron beams can penetrate.

The holding frame has a cavity 121 through which a cooling fluid can flow. The cavity 121 is located completely within the holding frame 120.

The cavity 121 is part of a separate cooling circuit 131 (see FIG. 1) through which a cooling fluid flows. The cooling circuit 131 can be part of the same cooling device 130 that cools the electron source 20 (see FIG. 1).

For example, the cavity 121 may contain liquid cooling fluid, while gas flows through the secondary channels 22.

FIG. 4 shows a perspective view of a second example of a cassette 24, which also shows the material channel 21, the two secondary channels 22 and the two protective elements 23.

The cavities are open to the secondary channels 22. Cooling fluid flowing through the secondary channels thus cools the holding frame 120 particularly effectively. The secondary channels 22 and the cavities 121 can be part of a cooling circuit 131 (see FIG. 1).

In this example, the protective element 23 contains several thickenings 122, which extend along a main plane of the protective element 23 and essentially perpendicular to a crop flow direction R. The thickenings 122 stabilize the protective element 23.

FIG. 5 shows a first perspective view of a third example of a cassette 124 of the inventional device 10.

The cassette 124 can be inserted in a direction S transverse to the direction of crop flow R into a not explicitly shown cassette receptacle of the device 10 (see FIG. 1) and has a handle 126 attached to a handle plate 127.

The material channel 21 and two secondary channels are formed in the cassette 124.

The cassette also includes as integral components two holding frames 120 for holding two protective elements not explicitly shown.

The cassette 124 and thus the holding frames 120 have a cavity 121 (see FIG. 2) for the passage of a cooling liquid. The cavity 121 is in the form of a continuous tube and is connected to a socket 125 for the introduction and discharge of the liquid. The connecting pieces 125 are designed as fluid connectors which can connect to a cooling circuit 131 (see FIG. 1).

FIG. 6 shows the same perspective view of the third example of a cassette 124 of the device according to the invention. In this view the handle plate 127 (see FIG. 5) is not shown. Therefore the cavity 121 is visible. This meanders as a groove through the cassette 124, which at the same time forms the holding frame 120 for the protective elements not explicitly shown.

After screwing or welding on the handle plate 127 (see FIG. 5), cavity 121 is a closed tube.

FIG. 7 shows the third example of a cassette 124 of the inventional device in a sectional view.

Cavity 121 is a closed tube leading from the nozzles 125 through the lower section 128 of cassette 124, past the handle plate 127 and back again. On the way between the nozzle 125 and the grip plate 127 the first holding frame 120 is cooled, on the way from the grip plate 127 back to the nozzles 125 the cavity 121 runs through the second holding frame 120.

The invention claimed is:

1. An apparatus for pasteurizing and/or sterilizing particulate material, comprising:
   at least two electron sources for generating an electron beam,
   a treatment zone, in which the material, freely falling, can be pasteurized and/or sterilized by means of the electron beam,
   a material channel arranged in a region of the treatment zone, in which the material can be pasteurized and/or sterilized by means of the electron beam, wherein the at least two electron sources are arranged opposite each other with respect to the freely falling material, two flat protective elements arranged between the at least two electron sources and the material channel, wherein each flat protective element is at least partially transparent to the electron beam, and the apparatus includes at least one holding frame which holds the two flat protective elements and which has a cavity through which a cooling fluid can flow, the apparatus comprising a cassette holder and a cassette with the at least one holding frame for the two flat protective elements, wherein the cassette contains the complete material channel.

2. The apparatus according to claim 1, wherein the two flat protective elements consist of a metal.

3. The apparatus according to claim 1, wherein the cavity is formed as a closed tube.

4. The apparatus according to claim 3, wherein the closed tube has a diameter of 3-8 mm.

5. The apparatus according to claim 1, wherein the two flat protective elements are formed as protective films.

6. The apparatus according to claim 1, wherein the apparatus has at least one secondary channel, through which a fluid can flow, which extends at least partially between the at least two electron sources and the material channel and is fluid-separated from the material channel.

7. The apparatus according to claim 6, wherein the two flat protective elements separate the material channel from the secondary channel.

8. The apparatus according to claim 6, wherein the secondary channel is arranged at least partially between the at least two electron sources and the two flat protective elements.

9. The apparatus according to claim 1, wherein each of the two flat protective elements comprises at least one thickening extending along a main plane of the flat protective element and substantially perpendicular to a material flow direction.

10. The apparatus according to claim 9, wherein the two flat protective elements are protective films.

11. The apparatus according claim 1, wherein the apparatus includes a cooling device with two interconnected cooling circuits, and a cooling fluid can be supplied to the at least one holding frame by a first cooling circuit and can be supplied to the at least two electron sources by a second cooling circuit.

12. The apparatus according to claim 1, the apparatus including at least one fan directed towards the two flat protective elements for further cooling the two flat protective elements.

13. The apparatus according to claim 1, wherein the at least one holding frame is an integral component of the cassette.

14. The apparatus according to claim 1, wherein the at least one holding frame is detachably received or receivable in the cassette.

15. The apparatus according to claim 1, wherein the cassette contains a pressure measuring device.

16. The apparatus according to claim 1, wherein the at least two electron sources are movable relative to the cassette holder in such a way that the at least two electron sources can be moved away from the cassette.

17. The apparatus according to claim 16, wherein the at least two electron sources are pivotable and/or displaceable.

18. The apparatus according to claim 1, wherein the cassette comprises a cavity, which is designed as a continuous tube and serves to cool both of the two flat protective elements and the cassette.

19. A method for pasteurizing and/or sterilizing particulate material with an apparatus according to claim 13, comprising the following steps:
   a) Generating an electron beam by means of the at least two electron sources,
   b) Pasteurization and/or sterilization of the material by means of the electron beam in the treatment zone, and
   c) Passing a cooling fluid through the cavity of the at least one holding frame to cool the two flat protective elements.

20. A method according to claim 19, wherein the cooling fluid has a temperature in a range of 15° C. to 43° C. when entering the cavity.

21. A method according to claim 19, whereby the cooling fluid is passed through the cavity with a volume flow in the range of 3 l/min to 5 l/min.

* * * * *